US00PP07972P

United States Patent [19]

Gressard

[11] Patent Number: Plant 7,972

[45] Date of Patent: Sep. 15, 1992

[54] ROSE PLANT — MARIBELL VARIETY

[75] Inventor: Jean Gressard, St Remy de Provence, France

[73] Assignee: Georges Delbard Société Civile Agricole, Malicorne, France

[21] Appl. No.: 578,573

[22] Filed: Sep. 7, 1990

[51] Int. Cl.[5] ..... A01H 5/00

[52] U.S. Cl. ..... Plt./12

[58] Field of Search ..... Plt./11, 12, 20, 21, Plt./22, 28, 29

[56] References Cited

U.S. PATENT DOCUMENTS

P.P. 2,549 8/1965 Boerner ..... Plt. 22

P.P. 4,437 7/1975 Warriner ..... Plt. 12

*Primary Examiner*—James R. Feyrer

*Attorney, Agent, or Firm*—Burns, Doane, Swecker & Mathis

[57] ABSTRACT

A new and distinct variety of Hybrid Tea rose plant is provided which abundantly forms attractive biocolored double flowers which are primarily deep red on the inside and white with red shadings which intensify uniformly towards the margins of the petals on the outside. Such flowers are long lasting and comprise petals which detach cleanly. The plant exhibits an upright growth, forms semivigorous vegetation, and is well suited for greenhouse forcing for cut flower production. Additionally, the plant is not particularly susceptible to diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parents (i.e., seed parent) of the new variety resulted from the crossing of the SEA PEARL variety with the ZORINA variety (U.S. Plant Pat. No. 2,321). The SEA PEARL variety sometimes is known as the FLOWER GIRL variety. The male parent (i.e., the pollen parent) was the LOVITA variety (U.S. Plant Pat. No. 2,598). The parentage of the new variety can be summarized as follows:

(SEA PEARL×ZORINA)×LOVITA.

The seeds resulting from the above pollination were sown and 153 small plantlets were obtained which were physically and biologically different from each other. Selective study resulted in the identification of a single plant of the new variety.

It was found through careful study that the new variety of the present invention can be characterized by the following combination of characteristics:

(a) from a physical point of view it forms bronze green mature wood, assumes an upright growth habit, and forms attractive biocolored double flowers having consistent petals which are primarily deep red on the inside and white with red shadings which intensify uniformly towards the margins of the petals on the outside, and (b) from the biological point of view it forms semivigorous vegetation, produces flowers in abundance, exhibits the ability readily to be forced, is not particularly susceptible to diseases, and forms long lasting flowers comprising petals which detach cleanly.

The new variety well meets the needs of the horticultural industry and is particularly well suited for the production of long-lasting cut flowers.

The new variety has been found to undergo asexual propagation and can be readily reproduced by bud grafting. The characteristics of the new variety have been found to be strictly transmissible by such asexual propagation from one generation to another.

The new variety has been named the MARIBELL variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass at Hyéres, France.

The single photograph shows from top to bottom the coloration of a growing tip and new growth; the upper surface of mature leaves having 3, 5 and 7 leaflets; the under surface of a mature leaf having 5 leaflets; mature stems stripped of leaves to depict the thorns; obverse and reverse views of flowers during the early and mid-opening stages; buds in the early and mid-opening expansion stages; a spent bloom with the sepals and stamens removed; and a spent bloom with sepals and stamens retained to clearly depict foliaceous appendages on the sepals and the arrangement of the stamens and pistils.

DETAILED DESCRIPTION

The chart used in the identification of the colors is that of The Royal Horticultural Society (R.H.S. Colour Chart). The description is based on the observation of plants grown under glass at Héres, France. The coloration in common terms sometimes also is provided.

Class: Hybrid tea.

Commercial class: Garden and greenhouse, cut flower.

Plant:

*Height.*—Plants which were pruned to a height of 85 cm. produce floral stems having a length of approximately 40 to 60 cm.

*Habit.*—Upright.

Branches:

*Color.*—Young shoots: when approximately 20 cm. long, exhibit a strong anthocyanin coloration having a purple hue. Mature wood: bronze green.

*Thorns.*—Configuration: concave on upper surface and deep concave on lower surface. Color: On young shoots: Greyed-Purple Group 183B. On mature wood: Greyed-Orange Group 166A and 166B. On floral stems: Greyed-Red Group 181A. Quantity: very few which are 5 mm. or less in length, and an average number which are greater than 5 mm. in length.

*Leaflets.*—Number: commonly 3, 5, and 7. Shape: oval as illustrated, substantially flat with a weak margin undulation. Serration: present. Texture: Consistent smooth. Color: Leaflets on young shoots: dark green, Yellow-Green Group 147A on the upper surface, and purple, Greyed-Purple Group 183B, on the under surface. Leaflets on mature wood: Green Group 137C on the upper surface, and Yellow-Green Group 147B and 147C on the under surface. Leaflets on floral stems: Yellow-Green Group 147A on upper surface, and Yellow-Green Group 147C on the under surface. Leaflet stems on young shoots: Greyed-Purple Group 187A and 187B when shoots are approximately 20 cm. in length. Leaflet stems on mature wood: Yellow-Green Group 146B and 146C. Leaflet stems on floral stems: Yellow-Green Group 146B with bronze coloration, Greyed-Purple Group 183A. General appearance: glossiness on the upper surface of the leaflets is either absent or very weak. Terminal leaflets: commonly range in length from approximately 54 to 96 mm. with a mean length of 69 mm. and a standard deviation of 11 mm.; commonly range in width from approximately 39 to 63 mm. with a mean width of 48 mm. and a standard deviation of 6 mm.; commonly exhibit a petiole length of approximately 15 to 26 mm. with a standard deviation of 3 mm.; have a obtuse base; and are borne on petioles of medium length.

Inflorescence:

*Number of flowers.*—Generally one per stem when forced in a greenhouse.

*Peduncle.*—Few hairs or prickles are present.

*Sepals.*—Configuration: very long with medium to long extensions.

*Buds.*—Shape: ovate in longitudinal section just before the opening of the sepals.

*Flower.*—Time: average time for beginning of flowering. Shape: double, irregularly rounded with viewed from above, a generally flattened convex upper surface when viewed from the side, and a generally convex under surface when viewed from the side. Diameter: commonly approximately 8.5 to 12 cm. with a mean diameter of 10.5 cm. and a standard deviation of 1 cm. Petal number: commonly 25 to 33 with an average of approximately 28. Petal size (second row from outside): commonly range in length from approximately 48 to 53 mm. with a mean length of 50 mm. and a standard deviation of 2 mm.; and commonly range in width from 46 to 51 mm. with a mean width of 48 mm. and a standard deviation of 2 mm. Petal shape: the first 2 to 3 well-developed outermost petals tend to be of a very broad obovate configuration and may be removed and discarded, the margins possess average reflexing, the margin undulation is weak, and include a yellowish unguis on both surfaces. Petal color: the middle and marginal zones of the inner side are deep red, near Red Group 46A, with occasional white flecks or short white striations, and finish after six days to near Red Group 53D; the outer side is substantially white with red shadings which intensify uniformly toward the margins of the petals, near Red Group 46A; a small spot of Yellow Group 4D is present on the inner side, and small spot of Yellow Group 2D is present on the outer side which finishes near white. Petal number: commonly approximately 25 to 33, and an average of 28. Petal drop: good and the petals drop off cleanly. Sepals: Color of upper surface: Yellow-Green Group 146B and 146C with Yellow-Green Group 147A on sepal extensions. Color on under surface: Yellow-Green Group 146B with Yellow-Green Group 147A and 147B on sepal extensions. Sepal extensions: vary in size from small to large and lack stipitate glands; occur irregularly along sepal margins and terminals; terminal appendages may be foliaceous and greatly extend the length and width of the sepals from which they arise. Fragrance: absent or very weak. Lasting Quality: long. Stamens: number approximately 160 on average and are regularly arranged around the pistils. Filaments: medium in length, most possess anthers, and the predominant coloration is yellow/white, Yellow Group 8B, 8C, 8D. Anthers: medium in size; tend to all open at approximately the same time; and the immature coloration is Yellow Group 8A. Pollen: very few pollen grains are formed and these are nearly white in coloration with a yellowish tint. Pistils: commonly approximately 93 on average. Stigmas: generally of approximately the same height as the anthers pale yellow, Yellow Group 10D. Styles: short in length and generally positioned just above the mouth of the receptacle, predominantly pink to purple in coloration, Red Purple Group 61C and with a strong concentration of pubescence on the upper one-half. Receptacle: medium in size, and in longitudinal section, it is in the shape of a pitcher. Hips: very few hips remain on the plant, commonly average approximately 20 mm., and are pitcher-shaped in configuration. Seeds: approximately 4 to 6 in number with an average of 5; medium in size; and commonly of an irregular configuration.

Development:

*Vegetation.*—Semi-vigorous when the plant is grown under greenhouse conditions and is pruned to a height of 85 cm. floral stems are formed having lengths of approximately 40 to 90 cm. with the mean length being approximately 70 cm.

*Blooming.*—Very abundant and nearly continuous.

*Resistance to forcing.*—Excellent.

*Resistance to diseases.*—Good.

It should be emphasized that the plants of the variety described herein were grown under glass for cut flower production. Generally one flower per stem is formed under forced greenhouse conditions. However, sometimes the first axillary eye below the terminal flower developes and may yield up to three flowers per stem. When the new variety is grown outside, multiple flowers per stem commonly are formed in a regular rounded cluster of approximately 3 to 13 blossoms, with the average number of blossoms being approximately 7 per stem.

I claim:

1. A new and distinct variety of hybrid tea rose plant characterized by the following combination of characteristics:

(a) from a physical point of view forms bronze green mature wood, assumes an upright growth habit, and forms attractive double flowers having consistent petals which are primarily deep on the inside and white with red shadings which intensify uniformly towards the margins of the petals on the outside, and (b) from the biological point of view forms semivigorous vegetation, produces flowers in abundance, exhibits the ability readily to be forced, is not particularly susceptible to diseases, and forms long lasting flowers comprising petals which detach cleanly;

substantially as herein shown and described.

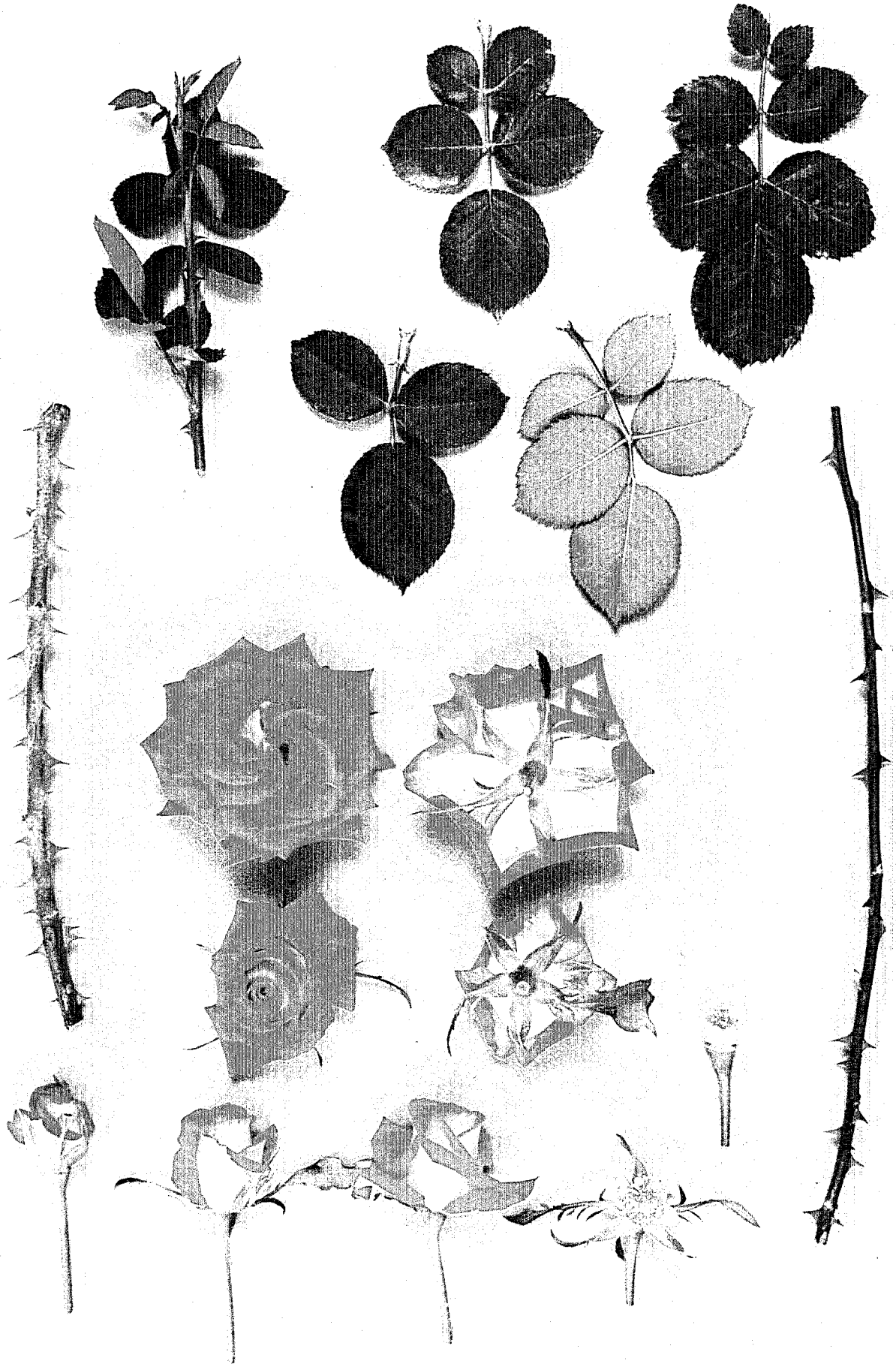

* * * * *